United States Patent [19]
Fearnot et al.

[11] Patent Number: 5,609,629
[45] Date of Patent: Mar. 11, 1997

[54] COATED IMPLANTABLE MEDICAL DEVICE

[75] Inventors: Neal E. Fearnot; Thomas G. Kozma; Anthony O. Ragheb; William D. Voorhees, all of West Lafayette, Ind.

[73] Assignee: MED Institute, Inc., West Lafayette, Ind.

[21] Appl. No.: 484,532

[22] Filed: Jun. 7, 1995

[51] Int. Cl.$^6$ .................................................. A61F 2/06
[52] U.S. Cl. .............................. 623/1; 623/11; 623/12; 604/53; 604/265
[58] Field of Search ........................ 623/1, 11, 12; 604/53, 265; 424/423, 426; 514/772.2, 772.3, 822; 523/112, 113

[56] References Cited

U.S. PATENT DOCUMENTS

| | | |
|---|---|---|
| 4,343,788 | 8/1982 | Mustacich et al. . |
| 4,479,795 | 10/1984 | Mustacich et al. . |
| 4,769,013 | 9/1988 | Lorenz et al. . |
| 5,053,048 | 10/1991 | Pinchuk . |
| 5,102,402 | 4/1992 | Dror et al. . |
| 5,217,493 | 6/1993 | Raad et al. . |
| 5,244,654 | 9/1993 | Narayanan . |
| 5,298,255 | 3/1994 | Sawamoto et al. . |
| 5,342,348 | 8/1994 | Kaplan . |
| 5,344,411 | 9/1994 | Domb et al. . |
| 5,345,933 | 9/1994 | Peterson et al. . |
| 5,380,299 | 1/1995 | Fearnot et al. . |
| 5,455,040 | 10/1995 | Marchant ................................ 623/1 |

Primary Examiner—John G. Weiss
Assistant Examiner—Francis K. Cuddihy
Attorney, Agent, or Firm—Richard J. Godlewski; Walter C. Danison

[57] ABSTRACT

A coated implantable medical device 10 includes a structure 12 adapted for introduction into the vascular system, esophagus, trachea, colon, biliary tract, or urinary tract; at least one layer 18 of a bioactive material positioned over the structure 12; and at least one porous layer 20 positioned over the bioactive material layer 18. Preferably, the structure 12 is a coronary stent, and the bioactive material is at least one of heparin, dexamethasone or a dexamethasone derivative. The device 10 includes layers 18 and 22 of heparin and dexamethasone, the layer 22 of dexamethasone being positioned above the layer 18 of heparin. The layers of bioactive material also can be individual materials or a combination of different materials. Unexpectedly, the more soluble heparin markedly promotes the release of the less soluble dexamethasone above it. The porous layer 20 is composed of a polymer applied by vapor or plasma deposition and provides a controlled release of the bioactive material. It is particularly preferred that the polymer is a polyimide, parylene or a parylene derivative, which is deposited without solvents, heat or catalysts, merely by condensation of a monomer vapor.

19 Claims, 2 Drawing Sheets

COATED IMPLANTABLE MEDICAL DEVICE

TECHNICAL FIELD

This invention relates generally to human and veterinary medical devices, and more particularly to devices incorporating drugs or bioactive agents.

BACKGROUND OF THE INVENTION

It has become common to treat a variety of medical conditions by introducing an implantable medical device partly or completely into the esophagus, trachea, colon, biliary tract, urinary tract, vascular system or other location within a human or veterinary patient. For example, many treatments of the vascular system entail the introduction of a device such as a stent, a catheter, a balloon, a wire guide, a cannula or the like. However, when such a device is introduced into and manipulated through the vascular system, the blood vessel walls can be disturbed or injured. Clot formation or thrombosis often results at the injured site, causing stenosis (closure) of the blood vessel. Moreover, if the medical device is left within the patient for an extended period of time, thrombus often forms on the device itself, again causing stenosis. As a result, the patient is placed at risk of a variety of complications, including heart attack, pulmonary embolism, and stroke. Thus, the use of such a medical device can entail the risk of precisely the problems that its use was intended to ameliorate.

Another way in which blood vessels undergo stenosis is through disease. Probably the most common disease causing stenosis of blood vessels is atherosclerosis. Atherosclerosis is a condition which commonly affects the coronary arteries, the aorta, the iliofemoral arteries and the carotid arteries. Atherosclerotic plaques of lipids, fibroblasts, and fibrin proliferate and cause obstruction of an artery or arteries. As the obstruction increases, a critical level of stenosis is reached, to the point where the flow of blood past the obstruction is insufficient to meet the metabolic needs of the tissue distal to (downstream of) the obstruction. The result is ischemia.

Many medical devices and therapeutic methods are known for the treatment of atherosclerotic disease. One particularly useful therapy for certain atherosclerotic lesions is percutaneous transluminal angioplasty (PTA). During PTA, a balloon-tipped catheter is inserted in a patient's artery, the balloon being deflated. The tip of the catheter is advanced to the site of the atherosclerotic plaque to be dilated. The balloon is placed within or across the stenotic segment of the artery, and then inflated. Inflation of the balloon "cracks" the atherosclerotic plaque and expands the vessel, thereby relieving the stenosis, at least in part.

While PTA presently enjoys wide use, it suffers from two major problems. First, the blood vessel may suffer acute occlusion immediately after or within the initial hours after the dilation procedure. Such occlusion is referred to as "abrupt closure." Abrupt closure occurs in perhaps five percent or so of the cases in which PTA is employed, and can result in myocardial infarction and death if blood flow is not restored promptly. The primary mechanisms of abrupt closures are believed to be elastic recoil, arterial dissection and/or thrombosis. It has been postulated that the delivery of an appropriate agent (such as an antithrombic) directly into the arterial wall at the time of angioplasty could reduce the incidence of thrombotic acute closure, but the results of attempts to do so have been mixed.

A second major problem encountered in PTA is the re-narrowing of an artery after an initially successful angioplasty. This re-narrowing is referred to as "restenosis" and typically occurs within the first six months after angioplasty. Restenosis is believed to arise through the proliferation and migration of cellular components from the arterial wall, as well as through geometric changes in the arterial wall referred to as "remodelling." It has similarly been postulated that the delivery of appropriate agents directly into the arterial wall could interrupt the cellular and/or remodelling events leading to restenosis. However, like the attempts to prevent thrombotic acute closure, the results of attempts to prevent restenosis in this manner have been mixed.

Non-atherosclerotic vascular stenosis may also be treated by PTA. For example, Takayasu arteritis or neurofibromatosis may cause stenosis by fibrotic thickening of the arterial wall. Restenosis of these lesions occurs at a high rate following angioplasty, however, due to the fibrotic nature of the diseases. Medical therapies to treat or obviate them have been similarly disappointing.

A device such as an intravascular stent can be a useful adjunct to PTA, particularly in the case of either acute or threatened closure after angioplasty. The stent is placed in the dilated segment of the artery to mechanically prevent abrupt closure and restenosis. Unfortunately, even when the implantation of the stent is accompanied by aggressive and precise antiplatelet and anticoagulation therapy (typically by systemic administration), the incidence of thrombotic vessel closure or other thrombotic complication remains significant, and the prevention of restenosis is not as successful as desired. Furthermore, an undesirable side effect of the systemic antiplatelet and anticoagulation therapy is an increased incidence of bleeding complications, most often at the percutaneous entry site.

Other conditions and diseases are treatable with stents, catheters, cannulae and other devices inserted into the esophagus, trachea, colon, biliary tract, urinary tract and other locations in the body, or with orthopedic devices, implants, or replacements. It would be desirable to develop devices and methods for reliably delivering suitable agents, drugs or bioactive materials directly into a body portion during or following a medical procedure, so as to treat or prevent such conditions and diseases, for example, to prevent abrupt closure and/or restenosis of a body portion such as a passage, lumen or blood vessel. As a particular example, it would be desirable to have devices and methods which can deliver an antithrombic or other medication to the region of a blood vessel which has been treated by PTA, or by another interventional technique such as atherectomy, laser ablation or the like. It would also be desirable that such devices would deliver their agents over both the short term (that is, the initial hours and days after treatment) and the long term (the weeks and months after treatment). It would also be desirable to provide precise control over the delivery rate for the agents, drugs or bioactive materials, and to limit systemic exposure to them. This would be particularly advantageous in therapies involving the delivery of a chemotherapeutic agent to a particular organ or site through an intravenous catheter (which itself has the advantage of reducing the amount of agent needed for successful treatment), by preventing stenosis both along the catheter and at the catheter tip. A wide variety of other therapies could be similarly improved. Of course, it would also be desirable to avoid degradation of the agent, drug or bioactive material during its incorporation on or into any such device.

SUMMARY OF THE INVENTION

The foregoing problems are solved and a technical advance is achieved in an illustrative vascular stent or other implantable medical device that provides a controlled release of an agent, drug or bioactive material into the vascular or other system, or other location in the body, in which a stent or other device is positioned. The agent, drug or bioactive material applied to a device can be degraded during application of a covering layer. Applicants have discovered that the degradation of an agent, a drug or a bioactive material applied to such a device can be avoided by covering the agent, drug or bioactive material with a porous layer of a biocompatible polymer that is applied without the use of solvents, catalysts, heat or other chemicals or techniques, which would otherwise be likely to degrade or damage the agent, drug or material. Those biocompatible polymers which can be applied by vapor deposition or plasma deposition, and which polymerize and cure merely upon condensation from the vapor phase, are expected to be useful for this purpose.

In a first aspect, then, the present invention is directed to an implantable medical device comprising a structure adapted for introduction into the esophagus, trachea, colon, biliary tract, urinary tract, vascular system or other location in a human or veterinary patient, the structure being composed of a base material; at least one layer of a bioactive material positioned over the structure; and at least one porous layer positioned over the bioactive material layer, the porous layer being composed of a polymer applied by vapor deposition or plasma deposition, and being of a thickness adequate to provide a controlled release of the bioactive material.

Preferably, when the device is intended for use in the vascular system, the bioactive material in the at least one layer is heparin or another antiplatelet or antithrombotic agent, or dexamethasone, dexamethasone acetate, dexamethasone sodium phosphate, or another dexamethasone derivative or anti-inflammatory steroid. Furthermore, a wide range of other bioactive materials can be employed, including, but not limited to, the following categories of agents: thrombolytics, vasodilators, antimicrobials or antibiotics, antimitotics, antiproliferatives, antisecretory agents, nonsteroidal antiinflammatory drugs, immunosuppressive agents, growth factor antagonists, free radical scavengers, antioxidants, biologic agents, radiotherapeutic agents, radiopaque agents and radiolabelled agents. The major restriction is that the bioactive material must be able to withstand the vacuum employed during vapor deposition or plasma deposition of the at least one porous layer, that is, the bioactive material must have a relatively low vapor pressure at the deposition temperature, typically, near or at room temperature.

The at least one porous layer is preferably composed of a polyimide, parylene or a parylene derivative applied by catalyst-free vapor deposition and is conveniently about 5,000 to 250,000 Å thick, which is adequate to provide a controlled release of the bioactive material. "Parylene" is both a generic name for a known group of polymers based on p-xylylene and made by vapor phase polymerization, and a name for the unsubstituted one of such polymers; the latter usage is employed herein. More particularly, parylene or a parylene derivative is created by first heating p-xylene or a suitable derivative at an appropriate temperature (for example, at about 950° C.) to produce the cyclic dimer di-p-xylylene (or a derivative of it). The resultant solid can be separated in pure form, and then cracked and pyrolyzed at an appropriate temperature (for example, at about 550° C.) to produce a monomer vapor of p-xylylene (or derivative); the monomer vapor is cooled to a suitable temperature (for example, below 50° C.) and allowed to condense on the desired object, for example, on the at least one layer of bioactive material. The resultant polymer has the repeating structure —$(CH_2C_6H_4CH_2-)_n$, with n equal to about 5,000, and a molecular weight in the range of 500,000.

As indicated, parylene and parylene derivative coatings applicable by vapor deposition are well known for a variety of biomedical uses, and are commercially available from or through a variety of sources, including Specialty Coating Systems (100 Deposition Drive, Clear Lake, Wis. 54005), Para Tech Coating, Inc. (35 Argonaut, Aliso Viejo, Calif. 92656) and Advanced Surface Technology, Inc. (9 Linnel Circle, Billerica, Mass. 01821-3902).

The at least one porous layer can alternatively be applied by plasma deposition. Plasma is an ionized gas maintained under vacuum and excited by electrical energy, typically in the radiofrequency range. Because the gas is maintained under vacuum, the plasma deposition process occurs at or near room temperature. Plasma can be used to deposit polymers such as poly(ethylene oxide), poly(ethylene glycol), poly(propylene oxide) and silicone, as well as polymers of methane, tetrafluoroethylene (including TEFLON brand polymers), tetramethyldisiloxane, and others.

The device can include two or more layers of different bioactive materials atop the structure. These additional layers can be placed directly atop one another or can be separated by additional porous polymer layers between each of them. Additionally, the layers of bioactive materials can comprise a mixture of different bioactive materials. The porous layers are also preferably composed of parylene or a parylene derivative. Advantageously, the two or more bioactive materials can have different solubilities, and the layer containing the less soluble bioactive material (for example, dexamethasone) is preferably positioned above the layer containing the more soluble bioactive material (for example, heparin). Unexpectedly, this has been found to increase the in vitro release rate of some relatively less soluble materials such as dexamethasone, while simultaneously decreasing the release rate of some relatively more soluble materials such as heparin.

In a particularly preferred aspect, the layer of bioactive material contains about 1 to 4 mg of the bioactive material per $cm^2$ of the gross surface area of the structure. "Gross surface area" refers to the area calculated from the gross or overall extent of the structure, and not necessarily to the actual surface area of the particular shape or individual parts of the structure.

While the structure included in the device can be configured in a variety of ways, the structure is preferably configured as a vascular stent composed of a biocompatible metal such as stainless steel, nickel, silver, platinum, gold, titanium, tantalum, iridium, tungsten, nitinol, inconel, or the like. An additional substantially nonporous coating layer of parylene or a parylene derivative about 50,000 to 500,000 Å thick can be positioned directly atop the vascular stent, beneath the at least one layer of bioactive material. The additional coating layer can merely be relatively less porous than the at least one porous layer, but preferably is substantially nonporous, that is, sufficiently nonporous to render the stent essentially impervious to blood during normal circumstances of use.

In a second aspect, the present invention is directed to a method of making an implantable medical device of the type disclosed above, in which the method comprises the steps of: positioning at least one layer of a bioactive material over the structure; and positioning at least one porous layer by vapor deposition or plasma deposition over the at least one bioactive material layer, the at least one porous membrane layer being composed of a polymer and being of a thickness adequate to provide a controlled release of the bioactive material. Conveniently, the at least one porous layer is polymerized from a monomer vapor which is free of any solvent or polymerization catalyst, and cures by itself upon condensation, without any additional heating or curing aid (for example, visible or ultraviolet light). The at least one layer of the bioactive material can be positioned over the structure by any convenient method such as dipping, rolling, brushing, spraying, electrostatic deposition, or the like.

Lastly, in a third aspect the present invention is directed to an improvement in a method of medically treating a human or veterinary patient by the step of inserting an implantable medical device, the device comprising a structure adapted for introduction into an applicable system of or location in the patient, and the structure being composed of a base material, in which the improvement comprises the preliminary steps of: positioning at least one layer of a bioactive material over the structure; and positioning at least one porous layer over the at least one bioactive material layer, the at least one porous layer being composed of a polymer, being of a thickness adequate to provide a controlled release of the bioactive material, and being applied by vapor deposition. The steps of the improvement are preferably carried out with the implantable medical device disclosed above.

The device and methods of the present invention are useful in a wide variety of locations within a human or veterinary patient, such as in the esophagus, trachea, colon, biliary tract, urinary tract and vascular system, as well as for orthopedic devices, implants or replacements. They are particularly advantageous for reliably delivering suitable bioactive materials during or following an intravascular procedure, and find particular use in preventing abrupt closure and/or restenosis of a blood vessel. More particularly, they permit the delivery of an antithrombotic, an antiplatelet, an anti-inflammatory steroid, an antithrombogenic or another medication to the region of a blood vessel which has been opened by PTA. The use of a porous polymer layer permits the release rate of a bioactive material to be carefully controlled over both the short and long terms. Most importantly, the use of a vapor or plasma deposited biocompatible polymer avoids any degradation of the bioactive material which might otherwise occur if the polymer layer had been deposited using solvents, catalysts, heating, or other chemicals or techniques.

BRIEF DESCRIPTION OF THE DRAWING

A better understanding of the present invention will now be had upon reference to the following detailed description, when read in conjunction with the accompanying drawing, wherein like reference characters refer to like parts throughout the several views, and in which.

DETAILED DESCRIPTION

Figure 1:
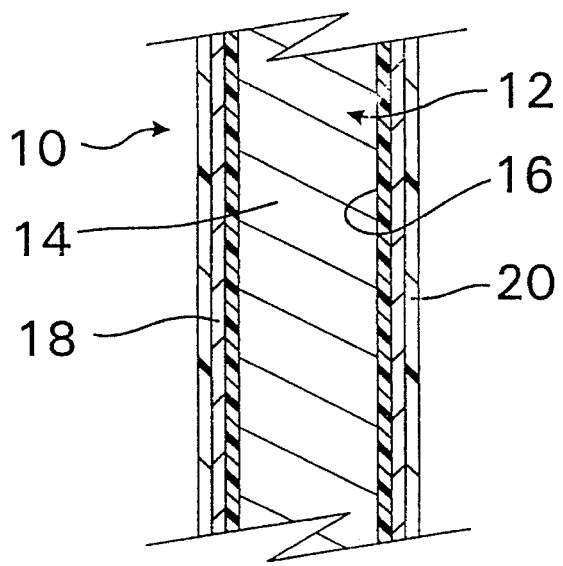
FIG. 1 is a cross-sectional view of a first preferred embodiment of the present invention.

With reference now to FIG. 1, an implantable medical device 10 in accordance with the present invention is thereshown and first comprises a structure 12 adapted for introduction into a human or veterinary patient. "Adapted" means that the structure 12 is shaped and sized for such introduction. For clarity, only a portion of the structure 12 is shown in FIG. 1.

By way of example, the structure 12 is configured as a vascular stent particularly adapted for insertion into the vascular system of the patient. However, this stent structure can be used in other systems and sites such as the esophagus, trachea, colon, biliary ducts, urethra and ureters, among others. Indeed, the structure 12 can alternatively be configured as any conventional vascular or other medical device, and can include any of a variety of conventional stent or other adjuncts, such as helically wound strands, perforated cylinders or the like. Moreover, because the problems addressed by the present invention arise with respect to those portions of the device actually positioned within the patient, the inserted structure 12 need not be an entire device, but can merely be that portion of a vascular or other device which is intended to be introduced into the patient. Accordingly, the structure 12 can be configured as at least one of, or any portion of, a catheter, a wire guide, a cannula, a stent, a vascular or other graft, a cardiac pacemaker lead or lead tip, a cardiac defibrillator lead or lead tip, a heart valve, a suture, a needle, an angioplasty device, a pacemaker or an orthopedic device, appliance, implant or replacement. The structure 12 can also be configured as a combination of portions of any of these.

Most preferably, however, the structure 12 is configured as a vascular stent such as the commercially available Gianturco-Roubin FLEX-STENT coronary stent from Cook Incorporated, Bloomington, Ind.. Such stents are typically about 10 to 60 mm in length and designed to expand to a diameter of about 2 to 6 mm when inserted into the vascular system of the patient. The Gianturco-Roubin stent in particular is typically about 12 to 25 mm in length and designed to expand to a diameter of about 2 to 4 mm when so inserted.

These stent dimensions are, of course, applicable to exemplary stents employed in the coronary arteries. Structures such as stents or catheter portions intended to be employed at other sites in the patient, such as in the aorta, esophagus, trachea, colon, biliary tract or urinary tract will have different dimensions more suited to such use. For example, aortic, esophageal, tracheal and colonic stents may have diameters up to about 25 mm and lengths about 100 mm or longer.

The structure 12 is composed of a base material 14 suitable for the intended use of the structure 12. The base material 14 is preferably biocompatible, although cytotoxic or other poisonous base materials may be employed if they are adequately isolated from the patient. Such incompatible materials may be useful in, for example, radiation treatments in which a radioactive material is positioned by catheter in or close to the specific tissues to be treated. Under most circumstances, however, the base material 14 of the structure 12 should be biocompatible.

A variety of conventional materials can be employed as the base material 14. Some materials may be more useful for structures other than the coronary stent exemplifying the structure 12. The base material 14 may be either elastic or inelastic, depending upon the flexibility or elasticity of the polymer layers to be applied over it. The base material may be either biodegradable or nonbiodegradable, and a variety of biodegradable polymers are known. Moreover, some biologic agents have sufficient strength to serve as the base material 14 of some useful structures 12, even if not especially useful in the exemplary coronary stent.

Accordingly, the base material 14 can include at least one of stainless steel, tantalum, titanium, nitinol, gold, platinum, inconel, iridium, silver, tungsten, or another biocompatible metal, or alloys of any of these; carbon or carbon fiber; cellulose acetate, cellulose nitrate, silicone, polyethylene teraphthalate, polyurethane, polyamide, polyester, polyorthoester, polyanhydride, polyether sulfone, polycarbonate, polypropylene, high molecular weight polyethylene, polytetrafluoroethylene, or another biocompatible polymeric material, or mixtures or copolymers of these; polylactic acid, polyglycolic acid or copolymers thereof, a polyanhydride, polycaprolactone, polyhydroxybutyrate valerate or another biodegradable polymer, or mixtures or copolymers of these; a protein, an extracellular matrix component, collagen, fibrin or another biologic agent; or a suitable mixture of any of these. Stainless steel is particularly useful as the base material 14 when the structure 12 is configured as a vascular stent.

Of course, when the structure 12 is composed of a radiolucent material such as polypropylene, polyethylene or others above, a conventional radiopaque coating may and preferably should be applied to it. The radiopaque coating provides a means for identifying the location of the structure 12 by X-ray or fluoroscopy during or after its introduction into the patient's vascular system.

With continued reference to FIG. 1, the vascular device 10 of the present invention next comprises at least one layer 18 of a bioactive material positioned over the structure 12. A vast range of drugs, medicants and materials can be employed as the bioactive material in the layer 18, so long as the selected material can survive exposure to the vacuum drawn during vapor deposition or plasma deposition. Particularly useful in the practice of the present invention are materials which prevent or ameliorate abrupt closure and restenosis of blood vessels previously opened by stenting surgery or other procedures. Thrombolytics (which dissolve, break up or disperse thrombi) and antithrombogenics (which interfere with or prevent the formation of thrombi) are especially useful bioactive materials when the structure 12 is a vascular stent. Particularly preferred thrombolytics are urokinase, streptokinase and the tissue plasminogen activators. Particularly preferred antithrombogenics are heparin, hirudin and the antiplatelets.

Urokinase is a plasminogen activating enzyme typically obtained from human kidney cell cultures. Urokinase catalyzes the conversion of plasminogen into the fibrinolytic plasmin, which breaks down fibrin thrombi.

Heparin is a mucopolysaccharide anticoagulant typically obtained from porcine intestinal mucosa or bovine lung. Heparin acts as a thrombin inhibitor by greatly enhancing the effects of the blood's endogenous antithrombin III. Thrombin, a potent enzyme in the coagulation cascade, is key in catalyzing the formation of fibrin. Therefore, by inhibiting thrombin, heparin inhibits the formation of fibrin thrombi.

Of course, bioactive materials having other functions can also be successfully delivered by the device 10 of the present invention. For example, an antiproliferative agent such as methotrexate will inhibit over-proliferation of smooth muscle cells and thus inhibit restenosis of the dilated segment of the blood vessel. The antiproliferative is desirably supplied for this purpose over a period of about four to six months. Additionally, localized delivery of an antiproliferative agent is also useful for the treatment of a variety of malignant conditions characterized by highly vascular growth. In such cases, the device 10 of the present invention could be placed in the arterial supply of the tumor to provide a means of delivering a relatively high dose of the antiproliferative agent directly to the tumor.

A vasodilator such as a calcium channel blocker or a nitrate will suppress vasospasm, which is common following angioplasty procedures. Vasospasm occurs as a response to injury of a blood vessel, and the tendency toward vasospasm decreases as the vessel heals. Accordingly, the vasodilator is desirably supplied over a period of about two to three weeks. Of course, trauma from angioplasty is not the only vessel injury which can cause vasospasm, and the device 10 may be introduced into vessels other than the coronary arteries, such as the aorta, carotid arteries, renal arteries, iliac arteries or peripheral arteries for the prevention of vasospasm in them.

A variety of other bioactive materials are particularly suitable for use when the structure 12 is configured as something other than a coronary stent. For example, an anti-cancer chemotherapeutic agent can be delivered by the device 10 to a localized tumor. More particularly, the device 10 can be placed in an artery supplying blood to the tumor or elsewhere to deliver a relatively high and prolonged dose of the agent directly to the tumor, while limiting systemic exposure and toxicity. The agent may be a curative, a pre-operative debulker reducing the size of the tumor, or a palliative which eases the symptoms of the disease. It should be noted that the bioactive material in the present invention is delivered across the device 10, and not by passage from an outside source through any lumen defined in the device 10, such as through a catheter employed for conventional chemotherapy. The bioactive material of the present invention may, of course, be released from the device 10 into any lumen defined in the device, or to tissue in contact with the device and that the lumen may carry some other agent to be delivered through it.

Dopamine or a dopamine agonist such as bromocriptine mesylate or pergolide mesylate is useful for the treatment of neurological disorders such as Parkinson's disease. The device 10 could be placed in the vascular supply of the thalamic substantia nigra for this purpose, or elsewhere, localizing treatment in the thalamus.

A wide range of other bioactive materials can be delivered by the device 10. Accordingly, it is preferred that the bioactive material contained in the layer 18 includes at least one of heparin or another thrombin inhibitor, hirudin, hirulog, argatroban, D-phenylalanyl-L-poly-L-arginyl chloromethyl ketone, or another antithrombogenic agent, or mixtures thereof; urokinase, streptokinase, a tissue plasminogen activator, or another thrombolytic agent, or mixtures thereof; a fibrinolytic agent; a vasospasm inhibitor; a calcium channel blocker, a nitrate, nitric oxide, a nitric oxide promoter or another vasodilator; an antimicrobial agent or antibiotic; aspirin, ticlopdine, a glycoprotein IIb/IIIa inhibitor or another inhibitor of surface glycoprotein receptors, or another antiplatelet agent; colchicine or another antimitotic, or another microtubule inhibitor, dimethylsulfoxide (DMSO), a retinoid or another antisecretory agent; cytochalasin or another actin inhibitor; or a remodelling inhibitor; deoxyribonucleic acid, an antisense nucleotide or another agent for molecular genetic intervention; methotrexate or another antimetabolite or antiproliferative agent; an anti-cancer chemotherapeutic agent; dexamethasone, dexamethasone sodium phosphate, dexamethasone acetate or another dexamethasone derivative, or another anti-inflammatory steroid or non-steroidal antiinflammatory agent; cyclosporin or another immunosuppressive agent; trapidal (a PDGF antagonist), angiopeptin (a growth hormone antagonist), an anti-growth factor antibody, or another growth factor antagonist; dopamine, bromocriptine mesylate, pergolide mesylate or another dopamine agonist; $^{60}$Co (5.3 year half life), $^{192}$Ir (73.8 days), $^{32}$P (14.3 days), $^{111}$In (68 hours), $^{90}$Y (64 hours), $^{99m}$Tc (6 hours) or another radiotherapetic agent; iodine-containing compounds, barium-containing compounds, gold, tantalum, platinum, tungsten or another heavy metal functioning as a radiopaque agent; a peptide, a protein, an enzyme, an extracellular matrix component, a cellular component or another biologic agent; captopril, enalapril or another angiotensin converting enzyme (ACE) inhibitor; ascorbic acid, alphatocopherol, superoxide dismutase, deferoxamine, a 21-aminosteroid (lasaroid) or another free radical scavenger, iron chelator or antioxidant; a $^{14}$C-, $^{3}$H-, $^{131}$I-, $^{32}$P- or $^{36}$S-radiolabelled form or other radiolabelled form of any of the foregoing; or a mixture of any of these.

When the structure 12 is configured as a vascular stent, however, particularly preferred materials for the bioactive material of the layer 18 are heparin, anti-inflammatory steroids including but not limited to dexamethasone and its derivatives, and mixtures of heparin and such steroids.

Still with reference to FIG. 1, the device 10 of the present invention also comprises at least one porous layer 20 positioned over the layer 18 of bioactive material. The purpose of the porous layer 20 is to provide a controlled release of the bioactive material when the device 10 is positioned in the vascular system of a patient. The thickness of the porous layer 20 is chosen so as to provide such control.

More particularly, the porous layer 20 is composed of a polymer deposited on the bioactive material layer 18 by the well-known process of vapor deposition. Plasma deposition is also useful for this purpose. Preferably, the layer 20 is one that is polymerized from a vapor which is free of any solvent, catalysts or similar polymerization promoters. Also preferably, the polymer in the porous layer 20 is one which automatically polymerizes upon condensation from the vapor phase, without the action of any curative agent or activity such as heating, the application of visible or ultraviolet light, radiation, ultrasound or the like. Optimally, the polymer in the porous layer 20 is polyimide, parylene or a parylene derivative.

When first deposited, the parylene or parylene derivative is thought to form a network resembling a fibrous mesh, with relatively large pores. As more is deposited, the porous layer 20 not only becomes thicker, but it is believed that parylene or parylene derivative is also deposited in the previously formed pores, making the existing pores smaller. Careful and precise control over the deposition of the parylene or parylene derivative therefore permits close control over the release rate of material from the at least one layer 18 of bioactive material. It is for this reason that the bioactive material lies under the at least one porous layer 20, rather than being dispersed within or throughout it. The porous layer 20, however, also protects the bioactive material layer 18 during deployment of the device 10, for example, during insertion of the device 10 through a catheter and into the vascular system or elsewhere in the patient.

As shown in FIG. 1, the device 10 of the present invention can further comprise at least one additional coating layer 16 positioned between the structure 12 and the at least one layer 18 of bioactive material. While the additional coating layer 16 can simply be a medical grade primer, the additional coating layer 16 is preferably composed of the same polymer as the at least one porous layer 20. However, the additional coating layer 16 is also preferably less porous than the at least one porous layer 20, and is more preferably substantially nonporous. "Substantially nonporous" means that the additional coating layer 16 is sufficiently impervious to prevent any appreciable interaction between the base material 14 of the structure 12 and the blood to which the device 10 will be exposed during use. The use of an additional coating layer 16 which is substantially nonporous would permit the use of a toxic or poisonous base material 14, as mentioned above. Even if the base material 14 of the structure 12 is biocompatible, however, it may be advantageous to isolate it from the blood by use of a substantially nonporous coating layer 16.

When the layer 18 of bioactive material contains a relatively soluble material such as heparin, and when the at least one porous layer 20 is composed of parylene or a parylene derivative, the at least one porous layer 20 is preferably about 5,000 to 250,000 Å thick, more preferably about 5,000 to 100,000 Å thick, and optimally about 50,000 Å thick. When the at least one additional coating layer 16 is composed of parylene or a parylene derivative, the at least one additional coating is preferably about 50,000 to 500,000 Å thick, more preferably about 100,000 to 500,000 Å thick, and optimally about 200,000 Å thick.

When the at least one layer 18 of bioactive material contains a relatively soluble material such as heparin, the at least one layer 18 preferably contains a total of about 1 to 4 mg of bioactive material per cm$^2$ of the gross surface area of the structure 12. This provides a release rate for the heparin (measured in vitro) which is desirably in the range of 0.1 to 0.5 mg/cm$^2$ per day, and preferably about 0.25 mg/cm$^2$ per day, under typical blood flows through vascular stents. It should be noted that the solubility of dexamethasone can be adjusted as desired, with or without the inclusion of heparin, by mixing it with one or more of its relatively more soluble derivatives, such as dexamethasone sodium phosphate.

Figure 2:
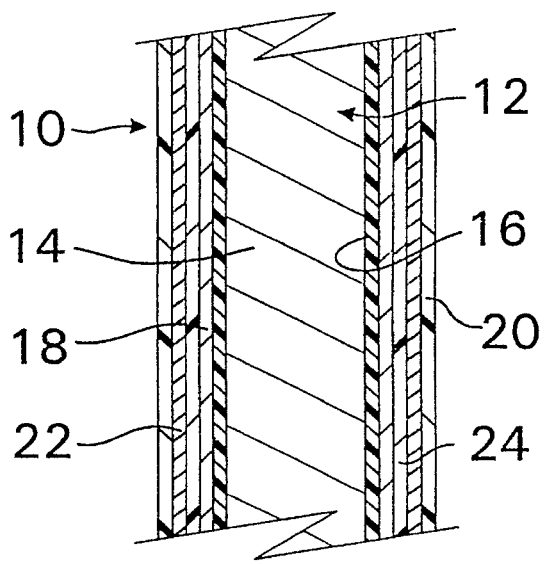
FIG. 2 is a cross-sectional view of another preferred embodiment of the present invention.

As shown in FIG. 2, the device 10 of the present invention is not limited to the inclusion of a single layer 18 of bioactive material. The device 10 can, for example, comprise a second layer 22 of a bioactive material positioned over the structure 12. The bioactive material of the second layer 22 can be, but need not necessarily be, different from the bioactive material of the first bioactive material layer 18. The use of different materials in the layers 18 and 22 allows the device 10 to perform more than a single therapeutic function.

The device 10 of the present invention can further comprise an additional porous layer 24 of the polymer positioned between each of the layers 18 and 22 of bioactive material. The additional porous layer 24 can give the bioactive materials in the layers 18 and 22 different release rates. Simultaneously, or alternatively, the device 10 can employ bioactive materials in the two layers 18 and 22 which are different from one another and have different solubilities. In such a case, it is advantageous and preferred to position the layer 22 containing the less soluble bioactive material above the layer 18 containing the more soluble bioactive material.

For example, when the structure 12 of the device 10 is configured as a vascular stent, it is advantageous for the at least one layer 18 to contain relatively soluble heparin, and the second layer 22 to contain relatively less soluble dexamethasone. Unexpectedly, the heparin promotes the release of the dexamethasone, increasing its release rate many times over the release rate of dexamethasone in the absence of heparin. The release rate of the heparin is also lowered, somewhat less dramatically than the increase of the dexamethasone release rate. More particularly, when dexamethasone is disposed by itself beneath a porous parylene layer 20 dimensioned as disclosed above, its release rate is negligible; an adequate release rate is obtained only when the thickness of the porous layer 20 is reduced by a factor of ten or more. In contrast, when a layer 22 of dexamethasone is disposed over a layer 18 of heparin, and beneath a porous parylene layer 20 dimensioned as above, the dexamethasone can released at a desirable rate of about 1 to 10 µg/cm$^2$ per day. Moreover, and even more unexpectedly, this increased release rate for the dexamethasone is thought to be maintained even after all of the heparin has been released from the layer 18.

The bioactive material layers 18 and/or 22 are applied to the device 10 independent of the application of the porous polymer layers 20 and/or 24. Any mixing of a bioactive material from the layers 18 and/or 20 into the porous layers 20 and/or 24, prior to introducing the device 10 into the vascular system of the patient, is unintentional and merely incidental. This gives significantly more control over the release rate of the bioactive material than the simple dispersal of a bioactive material in a polymeric layer.

Figure 3:
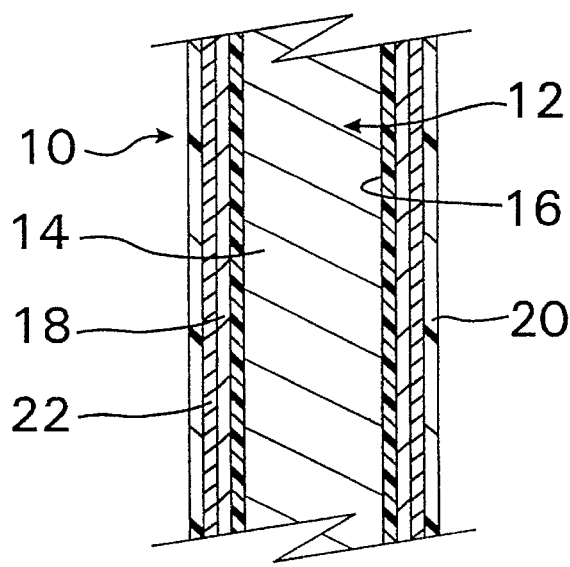
FIG. 3 is a cross-sectional view of yet another preferred embodiment of the present invention.

The device 10 need not include the additional porous layer 24 when two or more layers 18 and 22 of bioactive material are present. As shown in FIG. 3, the layers 18 and 22 do not have to be separated by a porous layer, but can instead lie directly against one another. It is still advantageous in this embodiment to position the layer 22 containing the relatively less soluble bioactive material above the layer 18 containing the relatively more soluble bioactive material.

Whether or not the additional porous layer 24 is present, it is preferred that the layers 18 and 22 contain about 0.5 to 2.0 mg of each of heparin and dexamethasone, respectively, per 1 cm$^2$ of the gross surface area of the structure 12. The total amount of bioactive material positioned in the layers 18 and 22 over the structure 12 is thus preferably in the range of about 1 to 4 mg/cm$^2$.

Some dexamethasone derivatives, such as dexamethasone sodium phosphate, are substantially more soluble than dexamethasone itself. If a more soluble dexamethasone derivative is used as the bioactive material in the device 10 of the present invention, the thickness of the at least one porous layer 20 (and of the additional porous layer 24) should be adjusted accordingly.

Of course, the particular structure of the device 10 as disclosed can be adapted to specific uses in a variety of ways. For example, the device 10 may include further layers of the same or different bioactive materials. These additional layers of bioactive material may or may not be separated by additional porous layers, as convenient or desired. Alternatively, additional porous layers may separate only some of the additional layers of bioactive material. Moreover, one bioactive material can be placed on one portion of the structure 12 of the device 10, and another bioactive material placed on a different portion of the structure 12 of the device 10.

Figure 4:
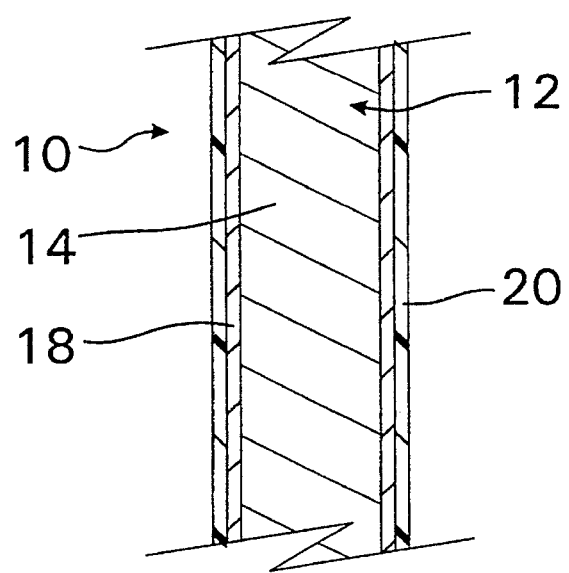
FIG. 4 is a cross-sectional view of a further preferred embodiment of the present invention.

Alternatively, the device 10 need not include the additional coating layer 16 at all. Such a configuration is shown in FIG. 4, in which the bioactive material layer 18 is positioned directly atop the base material 14 of the structure 12. In such a case, it may be highly advantageous to surface process or surface activate the base material 14, to promote the deposition or adhesion of the bioactive material on the base material 14, especially before the positioning of the at least one porous layer 20. Surface processing and surface activation can also selectively alter the release rate of the bioactive material. Such processing can also be used to promote the deposition or adhesion of the additional coating layer 16, if present, on the base material 14. The additional coating layer 16 itself, or any second or additional porous layer 24 itself, can similarly be processed to promote the deposition or adhesion of the bioactive material layer 18, or to further control the release rate of the bioactive material.

Useful methods of surface processing can include any of a variety of well-known procedures, including: cleaning; physical modifications such as etching or abrasion; and chemical modifications such as solvent treatment, the application of primer coatings, the application of surfactants, plasma treatment, ion bombardment and covalent bonding.

It has been found particularly advantageous to plasma treat the additional coating layer 16 (for example, of parylene) before depositing the bioactive material layer 18 atop it. The plasma treatment improves the adhesion of the bioactive material, increases the amount of bioactive material that can be deposited, and allows the bioactive material to be deposited in a more uniform layer. Indeed, it is very difficult to deposit a hygroscopic agent such as heparin on an unmodified parylene surface, which is hydrophobic and poorly wettable. However, plasma treatment renders the parylene surface wettable, allowing heparin to be easily deposited on it.

Any of the porous polymer layers 20 and 24 may also be surface processed by any of the methods mentioned above to alter the release rate of the bioactive material or materials, and/or otherwise improve the biocompatibility of the surface of the layers. For example, the application of an overcoat of polyethylene oxide, phosphatidylcholine or covalently attached heparin to the layers 20 and/or 24 could render the surface of the layers more blood compatible. Similarly, the plasma treatment or application of a hydrogel coating to the layers 20 and/or 24 could alter their surface energies, preferably providing surface energies in the range of 20 to 30 dyne/cm, thereby rendering their surfaces more biocompatible.

Figure 5:
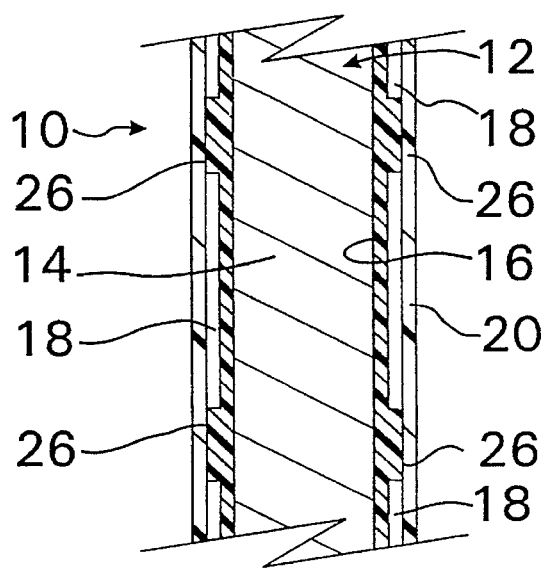
FIG. 5 is a cross-sectional view of an additional preferred embodiment of the present invention.

Referring now to FIG. 5, an embodiment of the device 10 is thereshown in which a mechanical bond or connector 26 is provided between (a) any one of the porous layers 20 and 24, and (b) any or all of the other of the porous layers 20 and 24, the additional coating layer 16 and the base material 14. The connector 26 reliably secures the layers 16, 20 and/or 24 to each other, and or to the base material 14. The connector 26 lends structural integrity to the device 10, particularly after the bioactive material layer or layers 18 and/or 20 have been fully released into the patient.

For simplicity, the connector 26 is shown in FIG. 5 as a plurality of projections of the base material 14 securing a single porous layer 20 to the base material 14. The connector 26 may alternatively extend from the porous layer 20, through the bioactive material layer 18, and to the base material 14. In either case, a single layer 18 of bioactive material, divided into several segments by the connector 26, is positioned between the porous layer 20 and the base material 14. The connectors can also function to partition the different bioactive agents into different regions of the device's surface.

The connector 26 can, of course, be provided in a variety of ways. For example, the connector 26 can be formed as a single piece with the base material 14 during its initial fabrication or molding into the structure 12. The connector 26 can instead be formed as a distinct element, such as a bridge, strut, pin or stud added to an existing structure 12. The connector 26 can also be formed as a built-up land, shoulder, plateau, pod or pan on the base material 14. Alternatively, a portion of the base material 14 between the desired locations of plural connectors 26 can be removed by etching, mechanical abrasion or the like, and the bioactive material layer 18 deposited between them. The connector 26 can also be formed so as to extend downwards towards the base material 14, by wiping or etching away a portion of a previously applied bioactive material layer 18, and allowing the porous layer 20 to deposit by vapor deposition or plasma deposition directly on the bare portions of the base material 14. Other ways to expose a portion of the base material 14 to direct connection to the porous layer 20 should be evident to those skilled in this area.

The method of making the device 10 according to the present invention may now be easily understood. In its simplest form, the method comprises the steps of positioning the at least one layer 18 of bioactive material over the structure 12, and positioning the at least one porous layer 20 by vapor deposition or plasma deposition over the at least one bioactive material layer 18, the at least one porous layer 20 being composed of a biocompatible polymer and being of a thickness adequate to provide a controlled release of the bioactive material. Preferably, the at least one additional coating layer 16 is first positioned by vapor deposition directly on the base material 14 of the structure 12. Such deposition is carried out by preparing or obtaining di-p-xylylene or a derivative thereof, sublimating and cracking the di-p-xylylene or derivative to yield monomeric p-xylylene or a monomeric derivative, and allowing the monomer to simultaneously condense on and polymerize over the base material 14. The deposition step is carried out under vacuum, and the base material 14 maintained at or near room temperature during the deposition step. The deposition is carried out in the absence of any solvent or catalyst for the polymer, and in the absence of any other action to aid polymerization. One preferred derivative for carrying out the deposition step is dichloro-di-p-xylylene. The parylene or parylene derivative is preferably applied at the thickness disclosed above, to yield a coating layer 16 which is substantially nonporous, but in any event less porous than the at least one porous layer 20 to be applied. If required by the composition of the coating layer 16, the layer 16 is then surface processed in an appropriate manner, for example, by plasma treatment as disclosed above.

The at least one layer 18 of the desired bioactive material or materials is then applied over the structure 12, and in particular, onto the additional coating layer 16. This application step can be carried out in any of a variety of convenient ways, such as by dipping, rolling, brushing or spraying a fluid mixture of the bioactive material onto the additional coating layer 16, or by electrostatic deposition of either a fluid mixture or dry powder of the bioactive material, or by any other appropriate method. Different bioactive agents can be applied to different sections or surfaces of the device.

It can be particularly convenient to apply a mixture of the bioactive material or materials and a volatile fluid over the structure, and then remove the fluid in any suitable way, for example, by allowing it to evaporate. When heparin and/or dexamethasone or its derivatives serve as the bioactive material(s), the fluid is preferably ethyl alcohol. The bioactive material is preferably applied in an amount as disclosed above.

Other methods of depositing the bioactive material layer 18 over the structure 12 would be equally useful. Without regard to the method of application, however, what is important is that the bioactive material need only be physically held in place until the porous layer 20 is deposited over it. This can avoid the use of carriers, surfactants, chemical binding and other such methods often employed to hold a bioactive agent on other devices. The additives used in such methods may be toxic, or the additives or methods may alter or degrade the bioactive agent, rendering it less effective, or even toxic itself. Nonetheless, if desired these other methods may also be employed to deposit the bioactive material layer 18 of the present invention.

The bioactive material may, of course, be deposited over the structure 12 as a smooth film or as a layer of particles and in a manner that different surfaces of the device contain different bioactive agents. In the latter case, the particle size may affect the properties or characteristics of the device 10, such as the smoothness of the uppermost porous coating 20, the profile of the device 10, the surface area over which the bioactive material layer 18 is disposed, the release rate of the bioactive material, the formation of bumps or irregularities in the bioactive material layer 18, the uniformity and strength of adhesion of the bioactive material layer 18, and other properties or characteristics. For example, it has been useful to employ micronized bioactive materials, that is, materials which have been processed to a small particle size, typically less than 10 µm in diameter. However, the bioactive material may also be deposited as microencapsulated particles, dispersed in liposomes, adsorbed onto or absorbed into small carrier particles, or the like.

In any event, once the bioactive material layer 18 is in place, the at least one porous layer 20 is then applied over the at least one bioactive material layer 18 in the same manner as for the application of the at least one additional coating 16. The polymer such as parylene or a parylene derivative is applied at the lesser thickness disclosed above, however, so as to yield the at least one porous layer 20.

Any other layers, such as the second bioactive material layer 22 or the additional porous layer 24, are applied in the appropriate order and in the same manner as disclosed above. The steps of the method are preferably carried out with any of the bioactive materials, structures, and base materials disclosed above.

Of course, polyimide can be deposited as any or all of the porous and additional coating layers 20, 24 and/or 16 by vapor deposition in a manner similar to that disclosed above for parylene and its derivatives. Techniques for the plasma deposition of polymers such as poly(ethylene oxide), poly(ethylene glycol), poly(propylene oxide), silicone, or a polymer of methane, tetrafluoroethylene or tetramethyl-disiloxane on other objects are well-known, and these techniques should be useful in the practice of the present invention.

The method of using the device 10 of the present invention in medically treating a human or veterinary patient can now be easily understood as well. The method of the present invention is an improvement in methods which include the step of inserting into a patient an implantable vascular device 10, the device 10 comprising a structure 12 adapted for introduction into the vascular system of a patient, and the structure 12 being composed of a base material 14. The improvement comprises the preliminary steps of positioning at least one layer 18 of a bioactive material over the structure 12, and positioning at least one porous layer 20 over the at least one bioactive material layer 18, the porous layer 20 being composed of a polymer and applied by vapor deposition, and being of a thickness adequate to provide a controlled release of the bioactive material when the device 10 is positioned in the patient's vascular system.

The method can further entail carrying out the two positioning steps with the various embodiments of the device 10 disclosed above, in accordance with the method of making the device 10 disclosed above. More particularly, the step of positioning the at least one porous layer 20 can comprise polymerizing the at least one layer 20 from a monomer vapor, preferably a vapor of parylene or a parylene derivative, free of any solvent or catalyst. The method can also comprise the step of positioning the at least one additional coating layer 16 between the structure 12 and the at least one bioactive material layer 18.

The method of treatment according to the present invention is completed by inserting the device 10 into the vascular system of the patient. The at least one porous layer 20 and any additional porous layers 24 automatically release the bioactive material or materials in a controlled fashion into the patient.

The remaining details of the method of medical treatment are the same as those disclosed with respect to the method of making the device 10 of the present invention; for the sake of brevity, they need not be repeated here.

In view of the disclosure above, it is clear that the present invention provides an implantable medical device which achieves precise control over the release of one or more bioactive materials contained in the device. Moreover, the polyimide, parylene, parylene derivative or other polymeric layers 16, 20 and/or 24 can be remarkably thin, in comparison to the thicknesses required for other polymer layers. The bulk or substantial majority of the overall coating on the structure 12 can therefore consist of bioactive material. This allows the supply of relatively large quantities of bioactive material to the patient, much greater than the amounts supplied by prior devices. These quantities of bioactive material can be supplied to any of a wide variety of locations within a patient during or after the performance of a medical procedure, but are especially useful for preventing abrupt closure and/or restenosis of a blood vessel by the delivery of an antithrombic or other medication to the region of it which has been opened by PTA. The invention permits the release rate of a bioactive material to be carefully controlled over both the short and long terms. Most importantly, any degradation of the bioactive material which might otherwise occur by other polymer coating techniques is avoided.

The other details of the construction or composition of the various elements of the disclosed embodiment of the present invention are not believed to be critical to the achievement of the advantages of the present invention, so long as the elements possess the strength or flexibility needed for them to perform as disclosed. The selection of these and other details of construction are believed to be well within the ability of one of even rudimentary skills in this area, in view of the present disclosure.

Industrial Applicability

The present invention is useful in the performance of vascular surgical procedures, and therefore finds applicability in human and veterinary medicine.

It is to be understood, however, that the above-described device is merely an illustrative embodiment of the principles of this invention, and that other devices and methods for using them may be devised by those skilled in the art, without departing from the spirit and scope of the invention. It is also to be understood that the invention is directed to embodiments both comprising and consisting of the disclosed parts. It is contemplated that only part of a device need be coated. Furthermore, different parts of the device can be coated with different bioactive materials or coating layers. It is also contemplated that different sides or regions of the same part of a device can be coated with different bioactive materials or coating layers.

What is claimed is:

1. An implantable medical device (10) comprising:
   a structure (12) adapted for introduction into a patient, the structure (12) being composed of a base material (14);
   at least one layer (18) of a bioactive material positioned over the structure (12);
   at least one porous layer (20) positioned over the bioactive material (18), composed of a polymer applied by vapored deposition or plasma deposition, and being of a thickness adequate to provide a controlled release of the bioactive material; and
   at least one additional coating layer (16) applied to the base material (14) and being less porous than, but composed of the same polymer as, at least one porous layer (20).

2. The device (10) according to claim 1, wherein the at least one porous layer (20) is one polymerized from a catalyst-free monomer vapor.

3. The device (10) according to claim 1, wherein the thickness of the at least one porous layer (20) is about 5,000 to 250,000 Å.

4. The device (10) according to claim 1, wherein the polymer is polyimide, parylene or a parylene derivative, and the at least one additional coating layer (16) is about 50,000 to 500,000 Å thick.

5. The device (10) according to claim 1, wherein the structure (12) is configured as a vascular stent.

6. The device (10) according to claim 1, wherein the structure (12) is configured as at least one of: a catheter, a wire guide, a cannula, a stent, a vascular or other graft, a cardiac pacemaker lead or lead tip, a cardiac defibrillator lead or lead tip, a heart valve, a suture, or a needle; an angioplasty device or portion thereof; a pacemaker or portion thereof; an orthopedic device, appliance, implant or replacement, or portion thereof; or a portion of any of these.

7. The device (10) according to claim 1, wherein the base material (14) is biocompatible.

8. The device (10) according to claim 1, wherein the base material (14) of the structure (12) includes at least one of: stainless steel, tantalum, titanium, nitinol, gold, platinum, inconel, iridium, silver, tungsten, or another biocompatible metal, or alloys of any of these; carbon or carbon fiber; cellulose acetate, cellulose nitrate, silicone, polyethylene teraphthalate, polyurethane, polyamide, polyester, polyorthoester, polyanhydride, polyether sulfone, polycarbonate, polypropylene, high molecular weight polyethylene, polytetrafluoroethylene, or another biocompatible polymeric material, or mixtures or copolymers of these; polylactic acid, polyglycolic acid or copolymers thereof, a polyanhydride, polycaprolactone, polyhydroxy-butyrate valerate or another biodegradable polymer, or mixtures or copolymers of these; a protein, an extracellular matrix component, collagen, fibrin or another biologic agent; or a mixture of any of these.

9. The device (10) according to claim 1, wherein the bioactive material includes at least one of: heparin or another thrombin inhibitor, hirudin, hirulog, argatroban, D-phenylalanyl-L-poly-L-arginyl chloromethyl ketone, or another antithrombogenic agent, or mixtures thereof; urokinase, streptokinase, a tissue plasminogen activator, or another thrombolytic agent, or mixtures thereof; a fibrinolytic agent; a vasospasm inhibitor; a calcium channel blocker, a nitrate, nitric oxide, a nitric oxide promoter or another vasodilator; an antimicrobial agent or antibiotic; aspirin, ticlopdine, a glycoprotein IIb/IIIa inhibitor or another inhibitor of surface glycoprotein receptors, or another antiplatelet agent; colchicine or another antimitotic, or another microtubule inhibitor, dimethylsulfoxide (DMSO), a retinoid or another antisecretory agent; cytochalasin or another actin inhibitor; or a remodelling inhibitor; deoxyribonucleic acid, an antisense nucleotide or another agent for molecular genetic intervention; methotrexate or another antimetabolite or antiproliferative agent; an anticancer chemotherapeutic agent; dexamethasone, dexamethasone sodium phosphate, dexamethasone acetate or another dexamethasone derivative, or another anti-inflammatory steroid or non-steroidal antiinflammatory agent; cyclosporin or another immunosuppressive agent; trapidal (a PDGF antagonist), angiopeptin (a growth hormone antagonist), an anti-growth factor antibody, or another growth factor antagonist; dopamine, bromocriptine mesylate, pergolide mesylate or another dopamine agonist; $^{60}$Co, $^{192}$Ir, $^{32}$P, $^{111}$In, $^{90}$Y, $^{99m}$Tc or another radiotherapeutic agent; iodine-containing compounds, barium-containing compounds, gold, tantalum, platinum, tungsten or another heavy metal functioning as a radiopaque agent; a peptide, a protein, an enzyme, an extracellular matrix component, a cellular component or another biologic agent; captopril, enalapril or another angiotensin converting enzyme (ACE) inhibitor; ascorbic acid, alphatocopherol, superoxide dismutase, deferoxamine, a 21-aminosteroid (lasaroid) or another free radical scavenger, iron chelator or antioxidant; a $^{14}$C-, $^{3}$H-, $^{131}$I-, $^{32}$P- or $^{36}$S-radiolabelled form or other radiolabelled form of any of the foregoing; or a mixture of any of these.

10. The device (10) according to claim 1, wherein the at least one layer (18) of bioactive material contains about 1 to 4 mg of the bioactive material per cm$^2$ of the gross surface area of the structure (12).

11. The device (10) according to claim 1, comprising at least two layers (18 and 22) of different bioactive materials positioned over the structure (12).

12. The device (10) according to claim 11, further comprising an additional porous layer (24) of the polymer between each of the at least two layers (18 and 22) of different bioactive materials.

13. The device (10) according to claim 11, wherein the at least two different bioactive materials have different solubilities, and the layer (22) containing the less soluble bioactive material is positioned above the layer (18) containing the more soluble bioactive material.

14. The device (10) according to claim 13, further comprising an additional porous layer (24) of the polymer between each of the at least two layers (18 and 22) of different bioactive materials.

15. The device (10) according to claim 1, further comprising a connector (26) securing the at least one porous layer (20) to the base material (14) of the structure (12).

16. An implantable medical device (10) comprising:

a structure (12) adapted for introduction into a patient, the structure (12) being composed of a base material (14);

at least one layer (18) of a bioactive material positioned over the structure (12);

at least one porous layer (20) positioned over the bioactive material (18), composed of a polymer applied by vapored deposition or plasma deposition, and being of a thickness adequate to provide a controlled release of the bioactive material; and wherein said device (10) comprises an additional layer of a different bioactive material (22) positioned over the structure (12).

17. The device (10) according to claim 16, further comprising an additional porous layer (24) of the polymer between each of the at least two layers (18 and 22) of different bioactive materials.

18. The device (10) according to claim 16, wherein the at least two different bioactive materials have different solubilities, and the layer (22) containing the less soluble bioactive material is positioned above the layer (18) containing the more soluble bioactive material.

19. The device (10) according to claim 16, further comprising an additional porous layer (24) of the polymer between each of the at least two layers (18 and 22) of different bioactive materials.

* * * * *